US012782288B2

(12) United States Patent
Gudmundsson et al.

(10) Patent No.: US 12,782,288 B2
(45) Date of Patent: Nov. 3, 2026

(54) SYSTEM AND METHOD FOR PERFORMING LASER-INDUCED BREAKDOWN SPECTROSCOPY MEASUREMENTS ON MOLTEN METAL SAMPLES

(71) Applicant: DTE EHF, Reykjavik (IS)

(72) Inventors: Sveinn Hinrik Gudmundsson, Mosfellsbaer (IS); Kristjan Leosson, Reykjavik (IS)

(73) Assignee: DTE EHF, Reykjavik (IS)

( * ) Notice: Subject to any disclaimer, the term of this patent is extended or adjusted under 35 U.S.C. 154(b) by 0 days.

(21) Appl. No.: 18/690,242

(22) PCT Filed: Sep. 7, 2022

(86) PCT No.: PCT/IS2022/050007
§ 371 (c)(1),
(2) Date: Mar. 7, 2024

(87) PCT Pub. No.: WO2023/037392
PCT Pub. Date: Mar. 16, 2023

(65) Prior Publication Data

US 2024/0426759 A1 Dec. 26, 2024

Related U.S. Application Data

(60) Provisional application No. 63/260,992, filed on Sep. 8, 2021.

(51) Int. Cl.
*G01N 33/205* (2019.01)
*G01N 21/71* (2006.01)

(52) U.S. Cl.
CPC ......... *G01N 21/718* (2013.01); *G01N 33/205* (2019.01); *G01N 2201/0221* (2013.01); *G01N 2201/1211* (2013.01)

(58) Field of Classification Search
CPC ......... G01N 2201/1211; G01N 21/718; G01N 33/205; G01J 3/443
See application file for complete search history.

(56) References Cited

U.S. PATENT DOCUMENTS

2003/0197125 A1* 10/2003 De Saro ............... G01N 33/205 378/53
2010/0085567 A1* 4/2010 Dottery .................. G01N 21/65 356/318
2016/0084709 A1* 3/2016 Day ...................... G01J 3/0272 356/318

FOREIGN PATENT DOCUMENTS

CN 108459012 A * 8/2018 ........... G01N 21/718
WO 2020239239 A1 12/2020

OTHER PUBLICATIONS

Rstoner88, "Melt Aluminum with coal", https://www.youtube.com/shorts/rfuF4Fdm4YE, Sep. 29, 2016 (Year: 2016).*
(Continued)

*Primary Examiner* — Maurice C Smith
(74) *Attorney, Agent, or Firm* — Tarolli, Sundheim, Covell & Tummino LLP

(57) ABSTRACT

LIBS measurement systems are disclosed that are configured to monitor the temperature of a molten metal sample during cooling of the molten metal sample in a crucible, and to initiate a LIBS measurement after the temperature of the molten metal sample satisfies measurement temperature criteria. The system may also monitor the temperature of an empty crucible to assist in ensuring that the crucible temperature is (i) sufficiently high to ensure that after the molten metal sample is delivered to the crucible and cools to satisfy the measurement temperature criteria, a sufficiently low cooling rate of the molten metal sample occurs during the LIBS measurement, and (ii) optionally sufficiently low to avoid an unnecessarily long cooling time of the molten
(Continued)

metal sample prior to satisfying the measurement temperature criteria and initiation of the LIBS measurement. The LIBS measurement system may be mobile and battery-powered, and may include an integrated calibration station.

41 Claims, 9 Drawing Sheets

(56) References Cited

OTHER PUBLICATIONS

Gruber J, Heitz J, Strasser H, Bauerle D, Ramaseder N. "Rapid in-situ analysis of liquid steel by laser-induced breakdown spectroscopy." Spectrochimica Acta Part B: Atomic Spectroscopy. Jun. 29, 2001;56(6):685-93.
Lin X, Chang P, Chen G, Lin J, Liu R, Yang H. "Effect of melting iron-based alloy temperature on carbon content observed in laser-induced breakdown spectroscopy." Plasma Science and Technology. Nov. 1, 2015;17(11):933.
Matiaske AM, Gornushkin IB, Panne U. "Double-pulse laser-induced breakdown spectroscopy for analysis of molten glass." Analytical and bioanalytical chemistry. Mar. 2012;402:2597-606.

* cited by examiner

SYSTEM AND METHOD FOR PERFORMING LASER-INDUCED BREAKDOWN SPECTROSCOPY MEASUREMENTS ON MOLTEN METAL SAMPLES

BACKGROUND

The present disclosure relates to the chemical analysis of liquid metals and alloys. More particularly, the present disclosure relates to use of laser-induced breakdown spectroscopy for the chemical composition analysis of liquid metals and alloys.

In metal production, monitoring the chemical composition of the produced metal is of critical importance. For example, in primary production of aluminum using continuous electrolysis according to the Hall-Héroult process, samples of metal from individual reduction cells are collected regularly for chemical analysis. This is done to monitor the level of impurities in the metal, which also serves as an indicator of the working condition of each cell.

A typical primary aluminum smelter will contain hundreds of reduction cells, from which samples are routinely collected (up to daily) during normal operation. The current standard practice involves extracting samples of liquid metal from the reduction cells and casting solid samples using standard sample molds, e.g. according to ASTM standard E716. The solid samples are subsequently analyzed for determining their chemical composition.

For decades, the standard method of analysis of solid samples in the aluminum industry has been spark atomic emission spectroscopy (also known as spark optical emission spectroscopy or spark-OES), e.g. according to ASTM standard E1251. Before performing spark-OES analysis, samples need to be suitably prepared, e.g., by mechanically milling to a certain depth into the cast sample. All the steps of sample preparation are important to ensure accurate analysis results.

SUMMARY

LIBS measurement systems are disclosed that are configured to monitor the temperature of a molten metal sample during cooling of the molten metal sample in a crucible, and to initiate a LIBS measurement after the temperature of the molten metal sample satisfies measurement temperature criteria. The system may also monitor the temperature of an empty crucible to assist in ensuring that the crucible temperature is (i) sufficiently high to ensure that after the molten metal sample is delivered to the crucible and cools to satisfy the measurement temperature criteria, a sufficiently low cooling rate of the molten metal sample occurs during the LIBS measurement, and (ii) optionally sufficiently low to avoid an unnecessarily long cooling time of the molten metal sample prior to satisfying the measurement temperature criteria and initiation of the LIBS measurement. The LIBS measurement system may be mobile and battery-powered, and may include an integrated calibration station.

Accordingly, in one aspect, there is provided a method of performing laser-induced breakdown spectroscopy (LIBS) on a molten sample during cooling of the molten sample, the method comprising:

monitoring a temperature of the molten sample during cooling of the molten sample within a crucible, and comparing the temperature of the molten sample to measurement temperature criteria; and determining that the temperature of the molten sample satisfies the measurement temperature criteria and initiating a LIBS measurement on the molten sample.

The method may further comprise, prior to introduction of the molten sample:

measuring, one or more times, a temperature of the crucible, the crucible being in a preheated state and absent of the molten sample, and comparing the temperature of the crucible to crucible temperature criteria; and determining that the temperature of the crucible satisfies the crucible temperature criteria and providing an indication that the crucible is ready to receive the molten sample;

wherein the crucible temperature criteria is configured such that the molten sample cools by fewer than 50° C. during the LIBS measurement.

In some example implementations of the method, the crucible temperature criteria comprises a minimum crucible temperature, such that the crucible temperature criteria is satisfied when the minimum crucible temperature is exceeded. The minimum crucible temperature may reside between 100° C. and 60% of the melting point temperature of the molten sample in degrees Celsius. The minimum crucible temperature may reside between 15% of the melting point temperature of the molten sample and 60% of the melting point temperature in degrees Celsius.

In some example implementations of the method, the crucible temperature criteria is satisfied when the temperature of the crucible resides within a crucible temperature range. A maximum crucible temperature of the crucible temperature range may be defined such that when the temperature of the crucible equals the maximum crucible temperature and the molten sample is added to the crucible, the temperature of the molten sample satisfies the measurement temperature criteria within 1 minute. A maximum crucible temperature of the crucible temperature range may be defined such that when the temperature of the crucible equals the maximum crucible temperature and the molten sample is added to the crucible, the temperature of the molten sample satisfies the measurement temperature criteria within 30 seconds. The maximum crucible temperature may reside between 50% of the melting point temperature of the molten sample in degrees Celsius and 90% of the melting point temperature.

In some example implementations of the method, the measurement temperature criteria is selected such that the LIBS measurement is performed within a pre-selected measurement temperature range.

In some example implementations of the method, the measurement temperature criteria comprises a pre-selected measurement temperature, and the LIBS measurement is initiated immediately after (i) determining that the temperature of the molten sample equals the pre-selected measurement temperature and (ii) positioning a LIBS measurement head over the crucible.

In some example implementations of the method, the measurement temperature criteria comprises a pre-selected measurement temperature, and the LIBS measurement is performed after determining that the temperature of the molten sample equals the pre-selected measurement temperature. The pre-selected measurement temperature may exceed the melting point temperature of the molten sample by an amount ranging from 5% to 25% of the melting point temperature in degrees Celsius.

In some example implementations of the method, the measurement temperature criteria comprises a pre-selected measurement temperature range, and the LIBS measurement is performed while the temperature of the molten sample resides within the pre-selected measurement temperature range.

In some example implementations of the method, the measurement temperature criteria is configured such that the temperature of the molten sample during the LIBS measurement exceeds the temperature of the crucible when the crucible temperature criteria is satisfied.

In some example implementations of the method, the crucible is preheated by a previously measured molten sample, wherein the previously measured molten sample is discarded prior to measuring the temperature of the crucible.

In some example implementations of the method, the molten sample comprises aluminum and the crucible is preheated by contact with a cryolite crust formed on the top of a reduction cell.

In some example implementations of the method, the temperature of the crucible and the temperature of the molten sample are measured using a common temperature sensor.

In some example implementations of the method, the temperature of the crucible and the temperature of the molten sample are measured in absence of contact.

In some example implementations of the method, the crucible is supported by a crucible support during LIBS measurement. LIBS measurements may be performed by a LIBS subsystem, and wherein a measurement head of the LIBS subsystem is movable from a parked position to an operative position in which the measurement head resides above the crucible support, and a heat shield is positioned to thermally shield the measurement head from heat radiating from the crucible when the measurement head resides in the parked position.

In some example implementations of the method, the crucible is a metallic crucible. The crucible may be formed from structural steel.

In some example implementations of the method, a heat capacity of the crucible resides between 400 and 500 J/K.

In some example implementations of the method, a thermal conductivity of the crucible resides between 40 and 50 W/m-K.

In some example implementations of the method, the crucible is a first crucible, the molten sample is a first molten sample, the method further comprising:

- discarding the first molten sample from the first crucible;
- measuring a temperature of the first crucible;
- determining that the temperature of the first crucible fails to satisfy the crucible temperature criteria due to an excessively high temperature;
- replacing the first crucible with a second crucible having a temperature less than that of the first crucible; and
- employing the second crucible to perform LIBS measurements on a second molten sample while cooling the first crucible.

The first crucible may be supported by a primary crucible support during the LIBS measurement performed on the first molten sample; and wherein, after replacing the first crucible with the second crucible, the first crucible is placed on a secondary crucible support for cooling.

In some example implementations, the method further comprises, prior to replacing the first crucible with the second crucible:

- preheating the second crucible;
- monitoring a temperature of the second crucible; and
- indicating when the second crucible satisfies the crucible temperature criteria.

In some example implementations, the method further comprises:

- optionally employing the second crucible to perform LIBS measurements on one or more additional molten samples;
- emptying the second crucible;
- measuring a temperature of the second crucible;
- determining that the temperature of the second crucible fails to satisfy the crucible temperature criteria due to an excessively high temperature; and
- replacing the second crucible with a crucible selected from:
  - the first crucible; and
  - a third crucible; and
- employing the selected crucible to perform LIBS measurements on another additional molten sample.

In some example implementations of the method, the LIBS measurement is performed by a LIBS system residing on a portable support structure, and the LIBS system is powered by a battery.

In another aspect, there is provided a method of performing laser-induced breakdown spectroscopy (LIBS) on a molten sample during cooling of the molten sample, the method comprising:

- preheating a crucible;
- introducing a molten sample into the crucible;
- monitoring a temperature of the molten sample during cooling of the molten sample within the crucible, and comparing the temperature of the molten sample to measurement temperature criteria; and
- determining that the temperature of the molten sample satisfies the measurement temperature criteria and initiating a LIBS measurement on the molten sample.

In some example implementations, the method further comprises, after preheating the crucible and prior to introduction of the molten sample into the crucible:

- measuring, one or more times, a temperature of the crucible, and comparing the temperature of the crucible to crucible temperature criteria; and
- determining that temperature of the crucible satisfies the crucible temperature criteria and providing the molten sample to the crucible;
- wherein the crucible temperature criteria is configured such that the molten sample cools by fewer than 50° C. during the LIBS measurement.

In another aspect, there is provided a system for performing laser-induced breakdown spectroscopy (LIBS), the system comprising:

- a temperature sensor; and
- a laser-induced breakdown spectroscopy (LIBS) subsystem; and
- processing circuitry operatively coupled to the temperature sensor and the LIBS subsystem, the processing circuitry comprising at least one processor and associated memory, the memory comprising instructions executable by the processor for performing operations comprising:
  - employing the temperature sensor to monitor a temperature of a molten sample during cooling of the molten sample within a crucible; and
  - determining that to the molten sample satisfies measurement temperature criteria and controlling the LIBS subsystem to initiate a LIBS measurement on the molten sample.

The processing circuitry may be further configured to perform the following operations prior to introduction of the molten sample into the crucible:

employing the temperature sensor to measure a temperature of the crucible, the crucible being preheated; and after determining that the temperature of the crucible satisfies crucible temperature criteria, providing an indication that the crucible is ready to receive the molten sample;

wherein the crucible temperature criteria is configured such that the molten sample cools by fewer than 50° C. during the LIBS measurement.

In another aspect, there is provided a portable system for performing laser-induced breakdown spectroscopy (LIBS), the portable system comprising:

a laser-induced breakdown spectroscopy (LIBS) subsystem comprising a measurement head, the LIBS subsystem being connectable to a battery;

a primary crucible support, wherein the measurement head of the LIBS subsystem is movable from a parked position to an operative position in which the measurement head resides above the primary crucible support for performing LIBS measurements on a molten sample residing in a crucible supported by the primary crucible support;

a secondary crucible support capable of supporting and cooling an additional crucible; and a mobile support structure configured to support the LIBS subsystem, the primary crucible support and the secondary crucible support.

In some example implementations, the system further comprises:

a temperature sensor configured to monitor a temperature of the crucible residing in the primary crucible support when the measurement head is in the parked position; and processing circuitry operatively coupled to the temperature sensor, the processing circuitry comprising at least one processor and associated memory, the memory comprising instructions executable by the processor for performing operations comprising:

employing the temperature sensor to measure a temperature of the crucible supported by the primary crucible support; and after determining that the temperature of the crucible fails to satisfy crucible temperature criteria due to an excessively high temperature, providing an indication that the crucible should be cooled in the secondary crucible support prior to use.

In some example implementations, the system further comprises the crucible and the additional crucible, wherein the crucible and the additional crucible are metallic. The crucible and the additional crucible may be formed from structural steel.

In some example implementations, the system further comprises the crucible and the additional crucible, wherein heat capacities of the crucible and the additional crucible reside between 400 and 500 J/K.

In some example implementations, the system further comprises the crucible and the additional crucible, wherein thermal conductivities of the crucible and the additional crucible reside between 40 and 50 W/m-K.

In another aspect, there is provided a portable system for performing laser-induced breakdown spectroscopy (LIBS), the portable system comprising:

a laser-induced breakdown spectroscopy (LIBS) subsystem comprising a measurement head, the LIBS subsystem being connectable to a battery;

an integrated calibration apparatus; and a mobile support structure configured to support the LIBS subsystem and the integrated calibration apparatus;

the measurement head of the LIBS subsystem being movable, from an operative position in which the measurement head resides above a crucible for performing LIBS measurements on a molten sample residing in the crucible, to a calibration position suitable for performing calibrating measurements suitable for calibrating at least one parameter of the LIBS subsystem.

In some example implementations of the system, the integrated calibration apparatus comprises a LIBS calibration reference material suitable for calibrating a signal of the LIBS subsystem when the measurement head resides in the calibration position. The integrated calibration apparatus may comprise a support frame, and wherein the LIBS calibration reference material is movable relative to the support frame such that when the measurement head is repositioned in the calibration position to perform a subsequent calibration measurement, a different region of the LIBS calibration reference material can be optically interrogated by the measurement head, thereby facilitating reuse of the LIBS calibration reference material during multiple calibration measurements.

In some example implementations of the system, the measurement head comprises a distance sensor, and wherein the integrated calibration apparatus is an integrated distance sensor calibration apparatus, the integrated distance sensor calibration apparatus comprising a contact location and a target location, the contact location being located on the integrated calibration apparatus such that when the measurement head resides at the calibration position and is contacted with the contact location after lowering the measurement head along a direction parallel to an optical axis of the measurement head, a known spatial offset resides between the distance sensor and the target location, thereby facilitating calibration of the distance sensor. The integrated distance sensor calibration apparatus may be elastically biased such that the known spatial offset is maintained when the measurement head is moved along the direction after having made contact with the contact location.

In some example implementations, the system further comprises:

a primary crucible support for supporting the crucible while performing the LIBS measurements; and a secondary crucible support capable of supporting and cooling an additional crucible.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1:
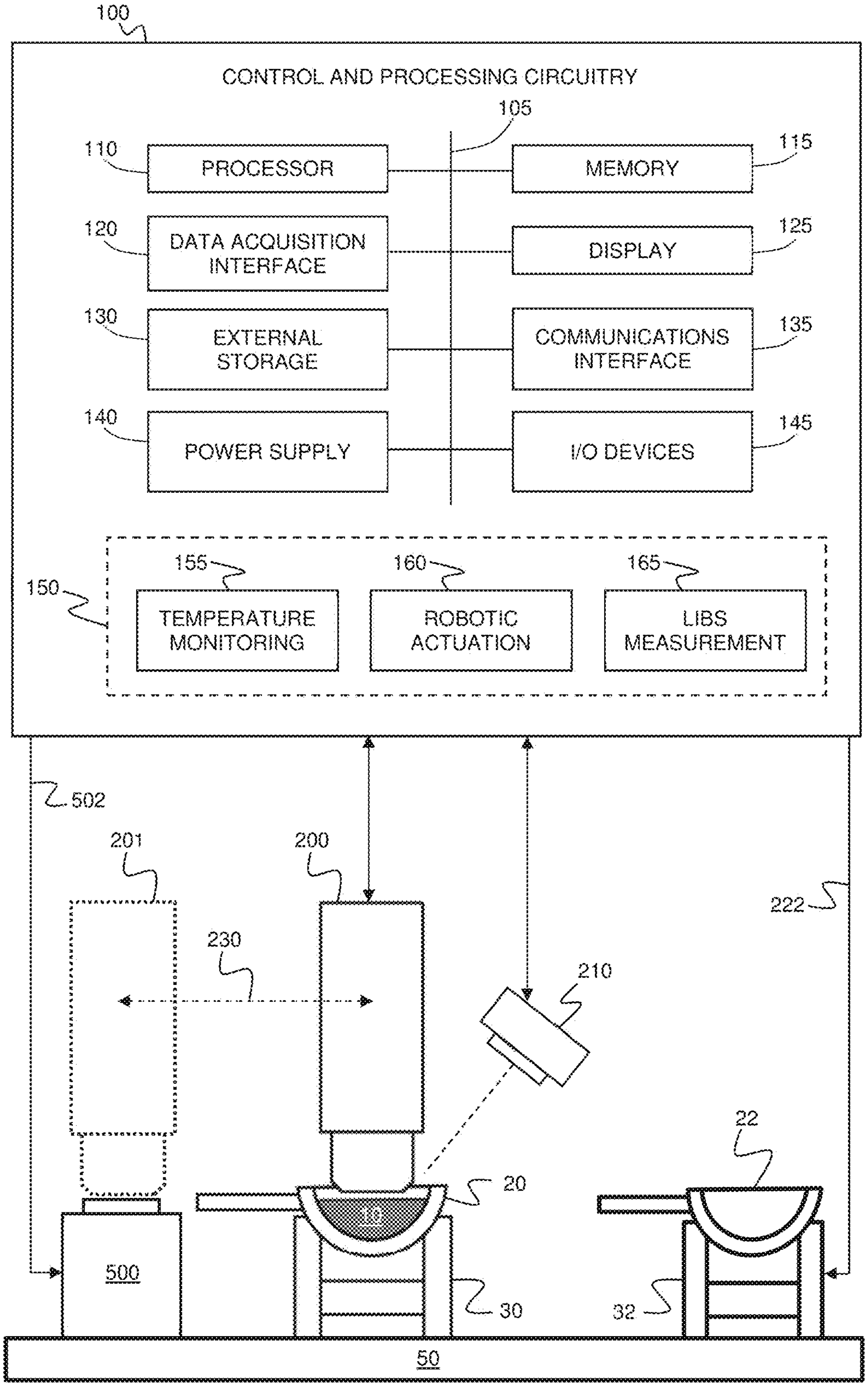
FIG. 1 shows an example system for performing LIBS measurements on molten metal samples.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

As used herein, percentage values associated with temperatures are intended to refer to temperatures in degrees Celsius.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As noted above, the conventional approach to chemical analysis in the aluminum industry employs the use of spark-OES on solid samples. Unfortunately, this conventional approach involves a number of technical problems that can impede the ability to achieve accurate chemical analyses.

In particular, the sample preparation process can lead to the introduction of errors. For example, errors may be introduced during the sample preparation process due to numerous potential causes, including, but not limited to, (i) temperature variations of the melt or mold when sampling is carried out, (ii) uneven pouring into sample molds, (iii) segregation related to the cooling rate of the metal, (iv) porosity, cracks or voids in the sample, (v) excessive surface roughness or smoothness after milling, and (vi) contamination of the surface before analysis.

Moreover, the conventional approach to casting samples and performing subsequent analysis can lead to the possibility of errors arising due to confusion between individual samples. Yet another problem associated with the conventional chemical analysis workflow is the safety hazard that can be caused by traffic inside the smelter that results from the transport of cast samples to a laboratory. Considering the steps of collecting liquid metal, casting solid samples, transporting samples to a central analysis facility, performing mechanical preparation and chemical analysis, hours may pass from the time that metal is sampled until analysis results are available to plant operators to make process decisions.

The present inventors, having identified and carefully considered the aforementioned technical and workflow challenges, set out to develop a new approach to chemical analysis that would overcome the problems associated with the conventional approach to chemical analysis. In particular, the present inventors recognized that in order to overcome these technical problems, a new chemical analysis modality would be needed that facilitates robust, rapid and accurate chemical testing in a real-time and in situ manner.

Various attempts have been made to adapt different detection modalities for real-time monitoring of the status of reduction cells in primary aluminum smelters. Some of these approaches include analysis of cell temperature and bath chemistry, analysis of individual anode current signals, analysis of cell voltage noise, and optionally a multiple of additional parameters affecting the current efficiency, energy consumption and operational lifetime of the cell. Differential thermal analysis has been successfully applied to determine bath chemistry, i.e., bath ratio and alumina ($Al_2O_3$) content, within a few minutes using, e.g., the commercially available STARprobe™ replacing the alternative time-consuming sample preparation and X-ray analysis in a central laboratory (X. Wang: "Alcoa STARprobe™—Update in Further development for measuring cryolite properties," TMS Light Metals 2016, pp. 397-402).

The real-time and in situ measurement of chemical impurities in the produced metal, however, presents a distinct challenge that is not addressed by the aforementioned real-time monitoring methods. Laser-induced breakdown spectroscopy (LIBS), an atomic emission spectroscopy technique applicable to the measurement of liquids and solids, has emerged as a promising technology for the chemical analysis of liquid metal. In particular, LIBS has previously been applied to measure the impurity content of liquid aluminum (A. K. Rai, F.-Y. Yueh, J. P. Singh: "Laser-induced breakdown spectroscopy of molten aluminum alloy," Appl. Opt. 42 (2003) pp. 2078-2084; J. Herbert, et al.: "The Industrial Application of Molten Metal Analysis," TMS Light Metals 2019, pp. 945-952; S. H. Gudmundsson, et al.: "Accurate Real-Time Elemental (LIBS) Analysis of Molten Aluminum and Aluminum Alloys," TMS Light Metals 2020, pp. 860-864.)

Attempts to adapt LIBS to real-time and in situ testing in industrial environments have been fraught with difficulties. For example, the complex and hazardous environment inside a primary aluminum smelter presents many technical challenges for the use of a LIBS system due to high temperatures, dust, and fumes emitted from the cells when opened. In addition, high magnetic fields present in the proximity of the reduction cells a challenge to operating measurement equipment (see, e.g., Sun et al., Spectrochimica Acta Part B 142 (2018) 29-36). While compact hand-held LIBS analyzers are available from several vendors, they are not suitable for analyzing liquid metal and do not provide the detection limits or accuracy required for monitoring aluminum from reduction cells.

Accordingly, despite the promise of LIBS for improved chemical composition analysis, there remains a need to solve outstanding technical challenges in order to facilitate the adaptation of LIBS to a real-time and in situ implementation that is sufficiently robust to deliver rapid and accurate chemical analysis of molten metals.

One problem encountered by the present inventors when attempting to adapt a LIBS measurement system in a portable configuration was the need to ensure a consistent measurement temperature of the molten metal sample during a LIBS measurement. Specifically, the relative intensities of LIBS emission lines can be dependent on sample temperature, with the consequence that variations in sample temperature among successive LIBS measurements can lead to significant errors in reported concentrations of impurities.

Although such a problem can potentially be addressed by actively controlling the temperature of the molten metal sample prior to or during LIBS measurement, such an approach can be problematic for a portable implementation due to the high power consumption of active heat sources, which can preclude the ability to power a portable system using batteries.

The present inventors sought to overcome these technical problems by developing a LIBS system that employs passive cooling of the molten metal sample, thus avoiding the need for active heating prior to, or during, the LIBS measurement. Moreover, it was determined that such an implementation could be adapted to facilitate accurate and repeatable LIBS measurements of subsequently measured samples without introducing significant measurement errors from variations in sample temperature, by monitoring the temperature of a molten metal sample during cooling of the molten metal sample and initiating a LIBS measurement when or after the monitored temperature satisfies pre-selected measurement temperature criteria. Such an implementation can be particularly beneficial in a mobile configuration due to the absence of a need for active heating of the molten metal sample prior to, and during, the LIBS measurement process, which can greatly simplify the system design and facilitate a battery-powered configuration. Furthermore, the implementation avoids having to introduce additional complications to the spectral analysis to detect and correct for the effects of temperature variation of the melt.

The monitoring of the temperature of the molten metal sample and initiation of the LIBS measurement only when measurement temperature criteria is satisfied ensures that LIBS measurements made on different molten metal samples (e.g. different samples from a common cell or different samples from different cells), which may have different initial temperatures, or different cooling rates due to different temperatures of the measurement crucible, are nonetheless performed at or near a common temperature during LIBS measurement. Such an example implementation thereby avoids, prevents or reduces measurement errors due to changes in sample temperature.

As will be described below, the present example embodiments can be beneficial in reducing the sources of error in analysis by analyzing the metal in the liquid state and by facilitating the immediate, direct, and unambiguous correlation of the chemical analysis results to a respective reduction cell. The present example systems and methods further facilitate a consistent and rapid workflow when measuring samples from multiple pots in sequence. Similarly, the present example systems and methods may be employed to facilitate rapid measurements of a series of samples extracted from a single reduction cell, or any similar manner in which multiple samples of liquid metal from a single source or a plurality of sources need to be analyzed in a rapid an accurate fashion.

Accordingly, in some example implementations, a portable chemical analysis system includes a LIBS measurement subsystem and a temperature sensor configured to monitor the temperature of a molten metal sample during passive cooling of the molten metal sample. The portable measurement system compares the measured temperature of the molten metal sample and controls the LIBS measurement subsystem to initiate the LIBS measurement after pre-selected measurement temperature criteria is satisfied.

An example embodiment of such a portable LIBS system is shown in FIG. 1. The example system includes a LIBS subsystem including a LIBS measurement head 200. The LIBS subsystem is operatively connected to, or connectable to, control and processing circuitry shown at 100, as described in further detail below. The LIBS measurement head 200 includes an optical beam delivery subsystem for delivering LIBS laser pulses onto the surface of a molten metal sample 10 and collecting optical emission from a plasma plume that is generated in response to interaction of the laser pulses with the target material. The LIBS measurement head 200 may include all sub-components of the LIBS system (including the LIBS laser source and detector). Alternatively, some of the components of the LIBS system (e.g. the LIBS laser source and/or detector) may be provided in a housing that is in optical and/or electrical communication with the LIBS measurement head 200.

Figure 2A:
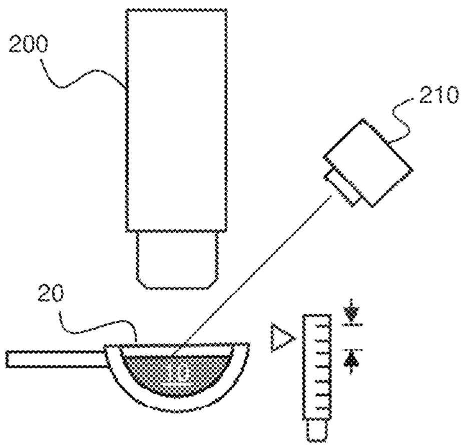
FIGS. 2A-2C show the monitoring of the temperature of the molten metal sample prior to initiation of LIBS measurements (FIG. 2A), the initiation of a LIBS measurement after determining that the temperature of the molten metal sample satisfies the measurement temperature criteria (FIG. 2B) and the measurement of an empty crucible prior to introduction of the molten metal sample.
Figure 2B:
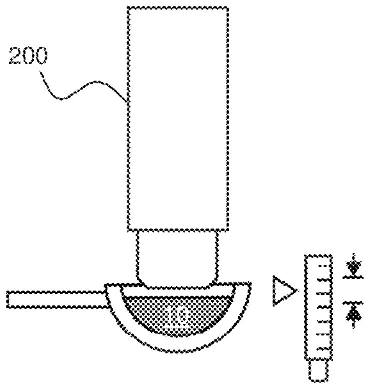

The molten metal sample 10 is passively cooled within a crucible 20 (e.g. ladle) prior to performing LIBS measurement while monitoring the temperature of the metal molten sample 10, as illustrated, for example, in FIG. 2A. As shown in FIG. 1, the crucible may be supported by a crucible support 30. When (or subsequent to) the temperature of the molten metal sample satisfies pre-selected measurement temperature criteria, the LIBS measurement is initiated, as shown in FIG. 2B.

Referring again to FIG. 1, the example system includes a temperature sensor 210 that is positionable to permit the interrogation of the surface of the molten metal sample 10. In some example implementations, the temperature sensor may be a non-contact temperature sensor such as, but not limited to, an infrared pyrometer or thermal camera. Such a sensor response can be corrected for the emissivity of the respective material being measured. Alternatively, the temperature sensor may be a contact-based temperature sensor, such as, but not limited to, a thermocouple or resistive thermometer.

The measurement temperature criteria ensures that LIBS measurements made on different molten metal samples (e.g. different samples from a common cell or different samples from different cells) are performed at or near the same temperature, thereby avoiding, preventing or reducing measurement errors due to changes in sample temperature, as discussed above. For example, the LIBS measurement head 200 may be controlled such that the LIBS measurement is initiated (i) immediately after the measurement temperature criteria is satisfied, (ii) after a fixed delay after the measurement temperature criteria is satisfied, or (iii) within a prescribed time interval after the measurement temperature criteria is satisfied, where said time interval may be calculated based on the observed cooling rate.

In one example implementation, the measurement temperature criteria may be satisfied when the measured temperature of the molten metal sample 10 reaches a measurement temperature, such as, for example, a measurement temperature exceeding the melting point temperature of the molten sample by 5%, or for example by 10%, or for example by 15%, or for example by 20%, or for example by 25%. In the example case of molten aluminum, a measurement temperature selected from the range of 700-800° C., such as 750° C.

In cases in which the LIBS measurement head 200 resides in a parked position (e.g. as shown at 201 in FIG. 1) during monitoring of the temperature of the molten metal sample 10 (e.g. in order to provide a sufficient line of sight for non-contact temperature sensing), the initiation of the LIBS measurement may include the repositioning of the LIBS measurement head 200 (e.g. as shown at 230 in FIG. 1) over the molten metal sample 10, optionally lowering the LIBS measurement head 200 relative to the surface of the molten metal sample 10, and subsequently delivering the LIBS laser pulses to the molten metal sample 10. Alternatively, in cases in which the temperature of the molten metal surface is measurable with the LIBS measurement head residing in a measurement position above the molten metal sample 10, the LIBS measurement may be initiated after the pre-selected measurement temperature criteria is satisfied by the measured temperature of the molten metal sample 10, without laterally moving the LIBS measurement head 200.

Prior to performing LIBS analysis, the surface of the molten metal sample may be skimmed with an automated skimmer (not shown in FIG. 1) or a manually operated skimmer. This skimming step serves to remove any dross or remaining bath material from the surface of the sample to expose the liquid metal for analysis as well as to ensure a proper measurement of the temperature of the liquid metal in the case of non-contact temperature measurement, as the dross formation will affect the emissivity of the sample surface. After performing the LIBS measurement, the LIBS measurement head 200 may be retracted (e.g. automatically), and the measurement results may be displayed and recorded (e.g. to a database). After LIBS analysis, the molten metal sample can be returned to the reduction cell, discarded elsewhere in liquid state or allowed to solidify and subsequently discarded or stored for reference. In some example implementations, a mobile analysis system may include an integrated disposal container for discarded samples.

It was found by the present inventors that the rate of cooling of the molten metal sample 10 during the LIBS measurement can impact the accuracy of the LIBS measurements. In particular, if the cooling rate is sufficiently high, the resulting temperature variation during the LIBS measurement step (which can involve a duration of several seconds, such as, for example, approximately 5 seconds) can lead to inaccuracies in the determination of impurity concentrations. Furthermore, a large variation in temperature during the LIBS measurement step can render the system susceptible to measurement errors if the timing of the LIBS measurement, relative to the time of determination of the measurement temperature criteria being satisfied, is not accurately controlled. Similarly, a high cooling rate can negatively impact the consistency of the measurement conditions of a series of measurements of different liquid metal samples.

This problem can be exacerbated when the crucible is made from a material that can lead to rapid cooling of the molten metal sample. For example, in order to facilitate rapid removal of the molten metal sample after LIBS measurement, it may be useful or necessary to contact the crucible with an impact surface to dislodge solidified metal from the crucible. In such cases, it may be beneficial to use a non-ceramic crucible that is capable of withstanding the impact without risk of breakage. One example of a suitable crucible is a metallic crucible, such as a crucible fashioned from structural steel. Given that such metallic crucibles typically have a high heat capacity and high thermal conductivity, it follows that a molten metal sample can rapidly cool within a cold metal crucible. In some example implementations, the heat capacity of such crucibles may reside between 400 and 500 J/K and the thermal conductivity of the crucible material may reside between 40 and 50 W/m-K.

In order to avoid or reduce errors induced by rapid cooling of the molten metal sample, the present inventors found that it can be beneficial to pre-heat the crucible 20 prior to delivery of the molten metal sample 10 to the crucible 20. Such pre-heating can be beneficial in reducing and/or controlling the rate of cooling of the molten metal sample 10 after the molten metal sample is received by the crucible 20. In addition, pre-heating improves the safety of the liquid metal sampling process by ensuring that crucibles are free of moisture before the introduction of liquid metal.

The preheating of the crucible can be performed according to a variety of methods. In some example embodiments, the preheating is performed external to the portable LIBS measurement system, such as by utilizing available heat from the reduction cells. For example, in an example implementation involving an aluminum smelter, the crucible may be preheated by placing it in contact with a cryolite crust formed inside the reduction cell for a sufficiently long period of time for the crucible to reach the desired temperature.

After pre-heating the crucible, the molten metal sample can be delivered to the crucible (e.g. measurement ladle). For example, a sample of liquid molten metal can be extracted using methods conventionally used for sampling metal from reduction cells, such as using a sampling ladle to collect molten metal from a reduction cell. For example, the sample of molten metal can be introduced manually to the sample crucible, e.g. by means of a human operator using such a sampling ladle. In addition, samples may be extracted, manually or automatically, from other types of sources such as a mixing furnace, holding furnace, or the like, where the sampling ladle can, in some embodiments, also be used as the sample crucible holding the sample during measurement.

In some example embodiments, it may be beneficial to ensure that the crucible 20 has been preheated by a sufficient amount to ensure that the cooling rate will not be inordinately rapid during the LIBS measurement. For example, prior to introducing the molten metal sample 10 into the crucible 20, the temperature of the crucible 20 may be measured and compared to crucible temperature criteria in order to evaluate whether or not the crucible 20 has been sufficiently pre-heated prior to receiving the molten metal sample 10. The measurement temperature criteria may be configured such that the temperature of the molten sample during the LIBS measurement exceeds the temperature of the crucible when the crucible temperature criteria is satisfied.

Figure 2C:
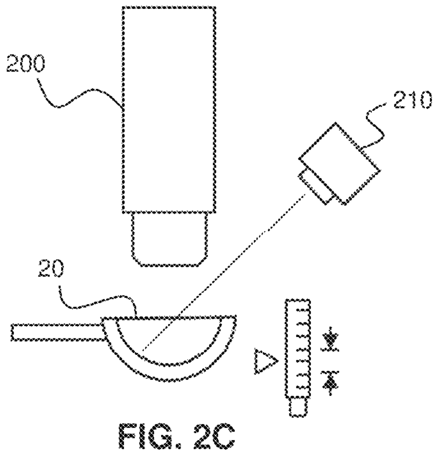

In some example implementations, the temperature sensor 210 that is employed to monitor the temperature of the molten metal sample 10 may be employed to measure the temperature of the empty crucible 20. Such an example implementation is illustrated in FIG. 2C. Alternatively, separate temperature sensors may be employed for monitoring the temperature of the molten metal sample and for measuring the temperature of the crucible 20 prior to delivery of the molten metal sample 10.

In some example embodiments, the crucible temperature criteria may be defined such that it is satisfied when the measured crucible temperature exceeds a pre-selected minimum temperature value, such as, for example, a minimum temperature that lies within the range of 100° C. to 60% of the melting point temperature of the molten metal, or for example, 15-60% of the melting point temperature (e.g. 100-400° C. in the case of aluminum), thereby ensuring that the cooling rate of the molten metal sample 10 after the molten metal sample 10 is delivered to the crucible 20 is kept within certain limits. For example, the crucible temperature criteria can be selected such that the molten metal sample cools by fewer than 50° C. during the LIBS measurement, or for example, cools by fewer than 20° C. during the LIBS measurement, or for example, cools by fewer than 10° C. during the LIBS measurement, or for example, cools by fewer than 5° C. during the LIBS measurement.

In the absence of an upper limit on the permissible initial temperature of the crucible 20, the crucible 20 may in some cases be preheated to a temperature that, while satisfying the crucible temperature criteria, is so high that an excessive amount of time will elapse before the molten metal sample 10 cools to a temperature that satisfies the measurement temperature criteria. In such cases, the time required for collecting and analyzing subsequent samples will be correspondingly increased. Such cases may be avoided by defining the crucible temperature criteria such that the crucible temperature criteria is not satisfied by a crucible temperature that exceeds an upper temperature value. For example, the crucible temperature criteria may include a maximum crucible temperature that is selected to lie within the range of 50-90% of the melting point temperature (e.g. between approximately 330 and 600° C. in the example case of aluminum). A maximum crucible temperature limit additionally ensures that the degree of contamination of crucible material into the molten metal is minimized.

For example, the crucible temperature criteria may be satisfied when the temperature of the crucible 20 (prior to receiving the molten metal sample 10) lies with a predefined temperature range, such as, for example, a range of 100° C. to 60% of the melting point temperature of the molten sample, or, for example, 15-60% of the melting point temperature (100-400° C. in the example case of aluminum) or a range of 30-75% of the melting point temperature (e.g. 200-500° C. in the example case of aluminum). The predefined temperature range may thus characterize a "Goldilocks" range, such that that when a molten metal sample 10 is delivered to a crucible satisfying the crucible temperature criteria, the molten metal cools at a rate that is sufficiently slow to permit accurate LIBS measurement (when the temperature of the molten metal sample satisfies the measurement temperature criteria) and such that the molten metal sample cools to a temperature that satisfies the measurement temperature criteria within a sufficiently short time duration. For example, the maximum temperature permitted by the crucible measurement criteria may be defined such that the molten metal sample, after having been delivered to the crucible, cools to a temperature that satisfies the measurement temperature criteria within 1 minute, or within 30 seconds, or within 15 seconds.

In some example implementations, an indication may be provided to an operator when the temperature of the empty crucible 20 satisfies the crucible temperature criteria. Non-limiting examples of suitable indications include a displayed message, symbol or colour, and an audible alarm or message. The indication may be employed to prompt an operator that the empty crucible 20 is ready to receive the molten metal sample. In other example implementations, the temperature of the empty crucible 20 may be displayed. In such cases, an operator having knowledge of suitable crucible temperature criteria (e.g. a minimum crucible or a desired crucible temperature range) may deliver the metal molten sample to the crucible when the displayed temperature satisfies the known crucible temperature criteria.

Figure 3:
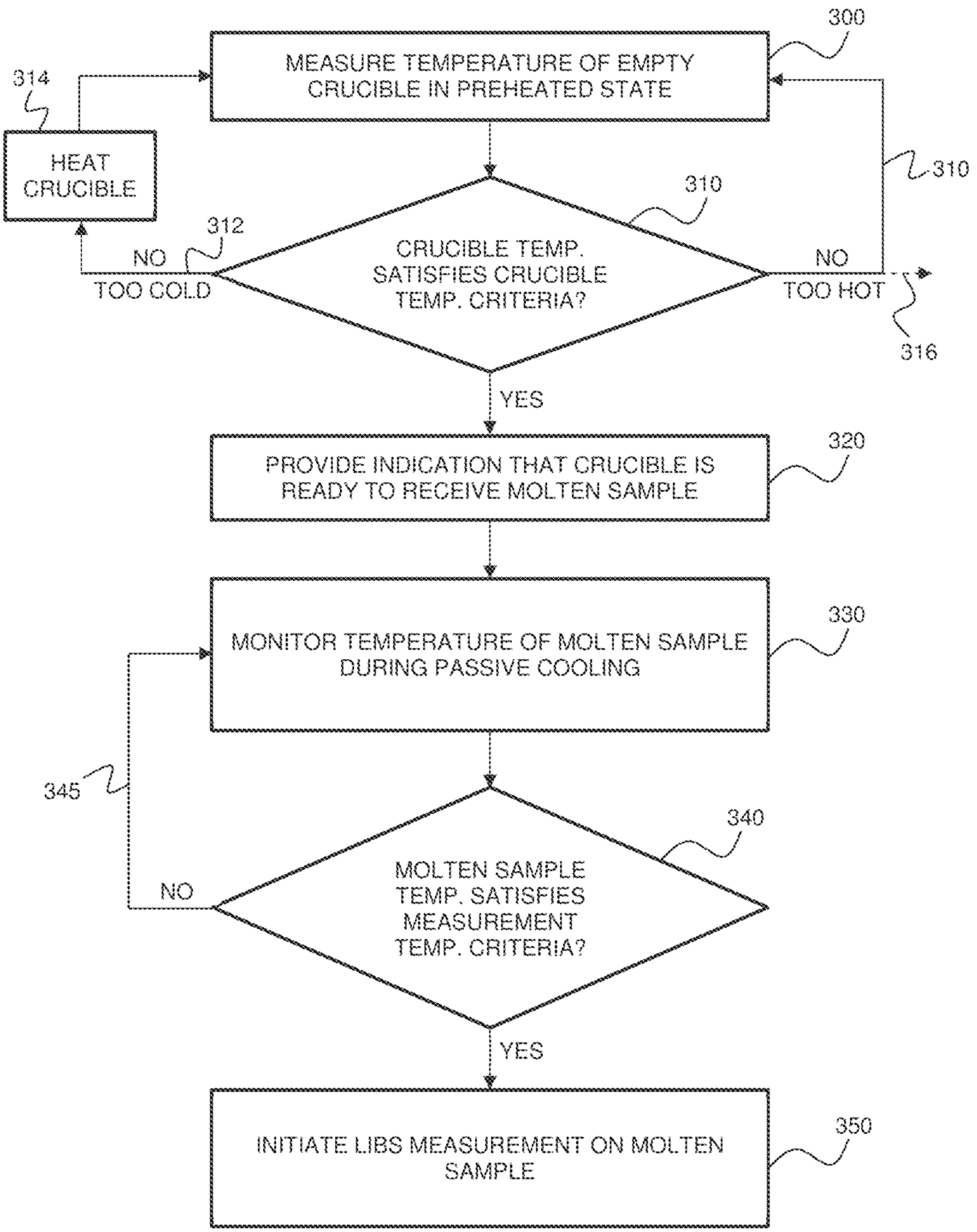
FIG. 3 is a flow chart illustrating an example method for performing LIBS measurements on molten metal samples utilizing passive cooling and temperature monitoring of the molten metal sample prior to initiation of the LIBS measurement.

Referring now to FIG. 3, a flow chart is provided that illustrates an example method of performing LIBS analysis of a molten sample using a LIBS measurement system such as the system illustrated in FIG. 1. A preheated empty crucible (absent of a molten metal sample) is initially provided and its temperature is measured at step 300. The crucible temperature criteria is evaluated at step 310. If the crucible criteria is not satisfied due to the crucible temperature being too low as shown at 312, the operator can heat the crucible, as shown at 314, and the crucible temperature can be re-measured and re-evaluated at 300. If the crucible temperature is too high, as shown at 310, the crucible can be left to passively cool, and the crucible temperature can be re-measured and re-evaluated at 300.

If the crucible temperature criteria is satisfied, an indication can be provided that the crucible is ready to receive the molten metal sample, as shown at 320. After the molten metal sample is received in the crucible, the temperature of the molten metal sample is monitored, as shown at 330, during cooling, and the measurement temperature criteria is evaluated as shown at 340. When the measurement temperature criteria is satisfied, the LIBS measurement is initiated, as shown at 350.

In the example method described above with reference to FIG. 3, the empty crucible is permitted to passively cool when its measured temperature fails to satisfy the crucible temperature criteria in step 310. For example, when a crucible is employed for multiple LIBS measurements, the crucible temperature can rise due to repeated exposure to hot molten metal samples, and the temperature of the crucible, after a previous molten metal sample is discarded, may exceed the maximum temperature permitted by the crucible temperature criteria. Unfortunately, as described above, the step of passively cooling such an overheated crucible may introduce an unwanted delay into the measurement process, especially when it is desirable to measure many samples in sequence with the lowest possible time delay between measurements.

Figure 5A:
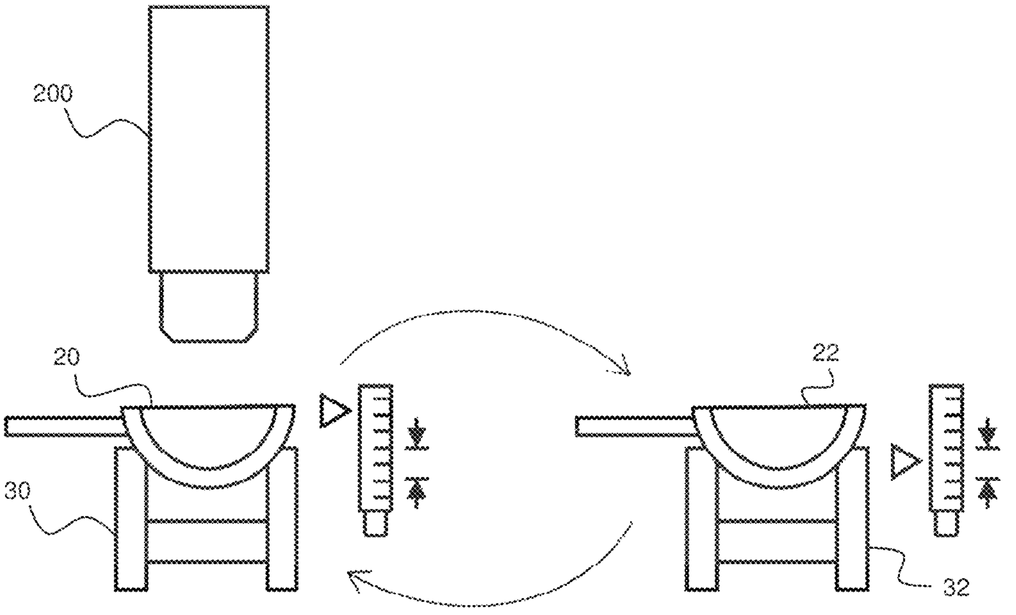
FIGS. 5A and 5B schematically illustrate the interchange of crucibles when a temperature of a given crucible is deemed to be too high for use in further measurements.

The problem associated with the delay in passive cooling an overheated crucible may be overcome by replacing the overheated crucible with a different crucible that has been preheated to a lower temperature. This process is schematically illustrated in FIG. 5A in which the overheated crucible 20 is replaced with a second preheated crucible 22.

Figure 4:
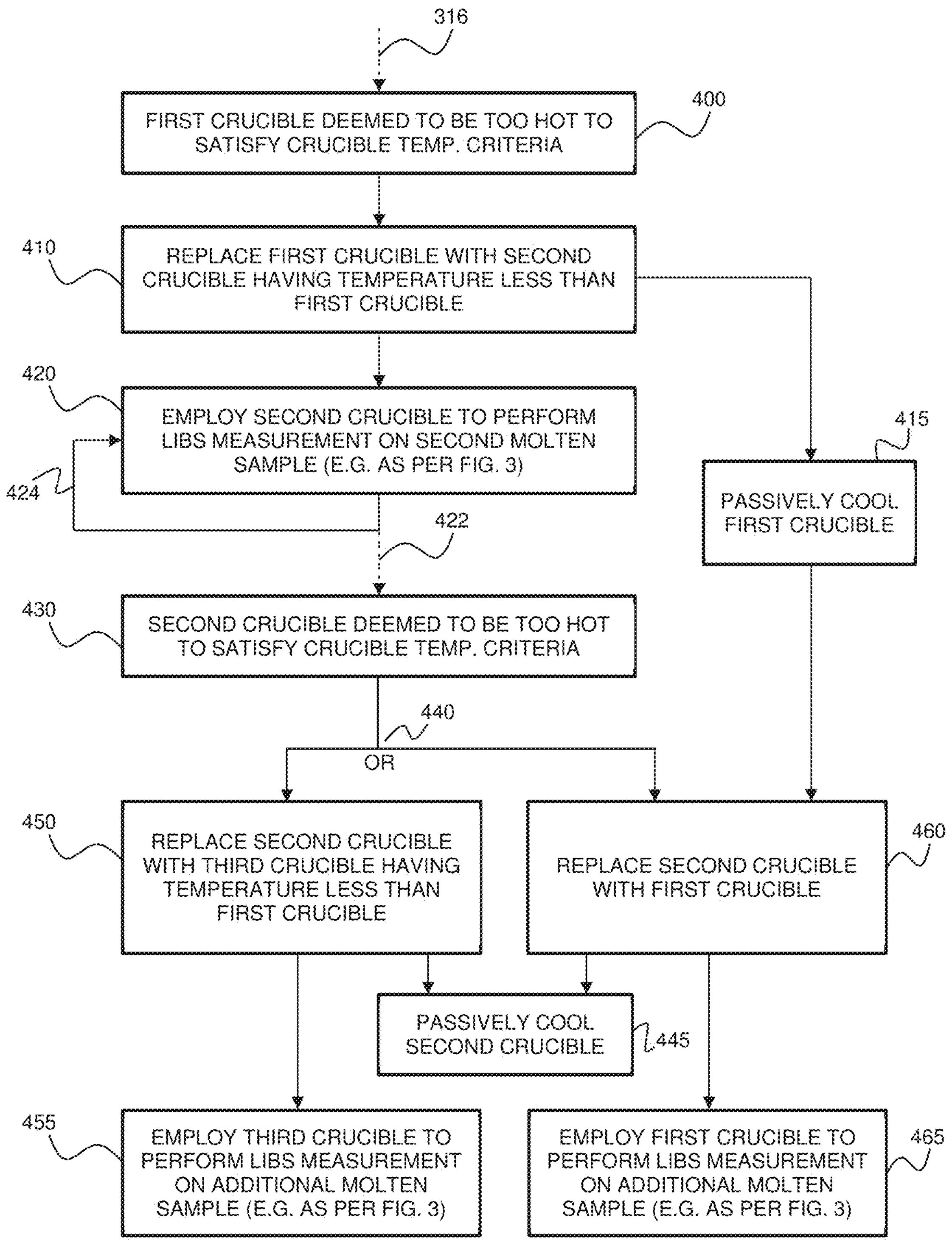
FIG. 4 is a flow chart illustrating an example method involving the replacement of an overheated crucible to minimize inter-measurement delay in a sequence of measurements.

FIG. 4 provides a flow chart illustrating an example method involving the replacement of an overheated crucible to minimize inter-measurement delay in a sequence of measurements. The example flow chart begins with step 316 from the flow chart in FIG. 3, corresponding to a determination that an empty crucible has a temperature that is too hot to satisfy the crucible temperature criteria, as shown at 400. This crucible is replaced with a second preheated crucible, as shown at 410. The second crucible may have a temperature that satisfies the crucible temperature criteria (as illustrated in FIG. 5A), or may have a temperature that exceeds a maximum permissible temperature of the crucible criteria, yet is less than the temperature of the first crucible, thereby resulting in a shorter time delay before the second crucible will cool to a temperature that satisfies the crucible temperature criteria.

The first (overheated) crucible, after having been replaced by the second crucible, may be supported on a crucible holder integrated with the LIBS measurement system (e.g. integrated with a common mobile support). As illustrated in FIG. 5A, the first crucible 20 may be placed onto the crucible support 32 (e.g. ladle support bracket) that had been previously employed to support the second crucible. Alternatively, the first crucible 20 may be placed onto a separate crucible support. The crucible support 32 may be configured such that its effective thermal mass, heat dissipation rate, and degree of thermal contact with the mounted crucible facilitates suitably rapid cooling of the crucible.

As shown at step 420 in FIG. 4, the second crucible is then employed to perform a LIBS measurement on a new molten metal sample, following steps 330-350 of FIG. 3. Furthermore, as shown at step 424, this process may be repeated one or more times for different samples, reusing the second crucible.

During use of the second crucible, the first crucible is supported by the additional crucible support 32 and passively cools from its initially overheated state. The temperature of the first crucible may be intermittently measured in order to determine when the first crucible again satisfies the crucible temperature criteria, as illustrated in FIG. 5A. For example, in cases in which the temperature sensor 210 is secured relative to the LIBS measurement head 200, the LIBS measurement head 200 may be translated to facilitate interrogation of the first crucible 20 residing in the crucible support 32 between use of the LIBS measurement head 200 for LIBS measurements. In an alternative example implementation, a separate temperature sensor may be provided for monitoring the temperature of the crucible residing in the additional crucible support 32. For example, a temperature sensor (e.g. such as, but not limited to, an infrared pyrometer or thermocouple sensor) may be integrated into the additional crucible support 32 for monitoring the temperature of the first crucible, as shown, for example, at 222 in FIG. 1. An indication may be provided to an operator when the first crucible again satisfies the crucible temperature measurement criteria. Alternatively, the temperature of the first crucible may be displayed to permit an operator to determine when the first crucible satisfies pre-determined crucible temperature criteria.

Referring again to FIG. 4, after repeated use of the second crucible, the temperature of the second crucible may no longer satisfy the crucible measurement criteria, and the second crucible may need to be cooled prior to further use. In such a case, rather than allowing the second crucible to passively cool until its temperature satisfies the crucible temperature criteria, the second crucible may be exchanged for another crucible.

Figure 5B:
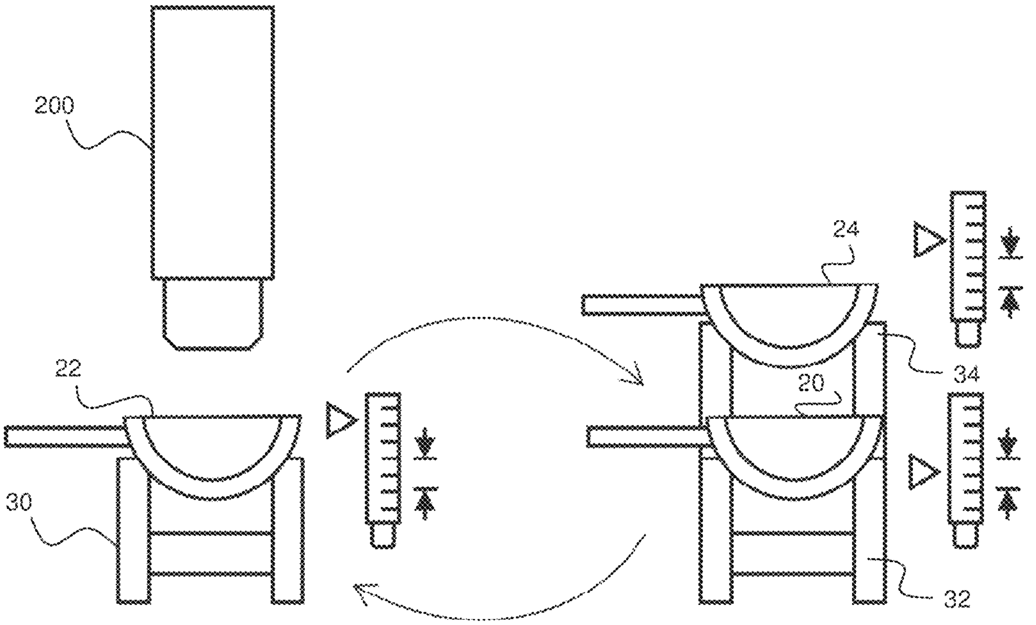

Step 450 illustrates an example scenario in which the second crucible is exchanged with a third crucible that has been preheated. Alternatively, as shown in step 460, the second crucible may be exchanged with the first crucible, since the first crucible will have cooled during the use of the second crucible for LIBS measurements. These options are schematically illustrated in FIG. 5B, which shows the second crucible 22 being exchanged with either the first crucible 20 or a third crucible 24 (residing on third crucible support 34). The second crucible may then be passively cooled, as shown at 445, while employing the first or third crucible to perform LIBS measurements on additional molten metal samples, as shown at steps 455 and 465, respectively.

While the preceding example implementations employ one or two additional crucible supports, three or more crucible supports may be included in order to provide additional locations for the cooling of crucibles. The number of crucible supports needed may depend on the rate of analysis and the need to ensure a continuous operation when measuring from multiple sampling points.

As explained above, in some example implementations, the LIBS measurement head 200 may reside in a parked position prior to performing LIBS analysis. For example, the LIBS measurement head may be translated (e.g. robotically translated) laterally and/or vertically to a parked position during monitoring of the molten metal sample in order to provide a sufficient line of sight for non-contact temperature sensing. The LIBS measurement head may also be translated to a parked position to perform one or more calibration steps, as described in further detail below.

Figure 6:
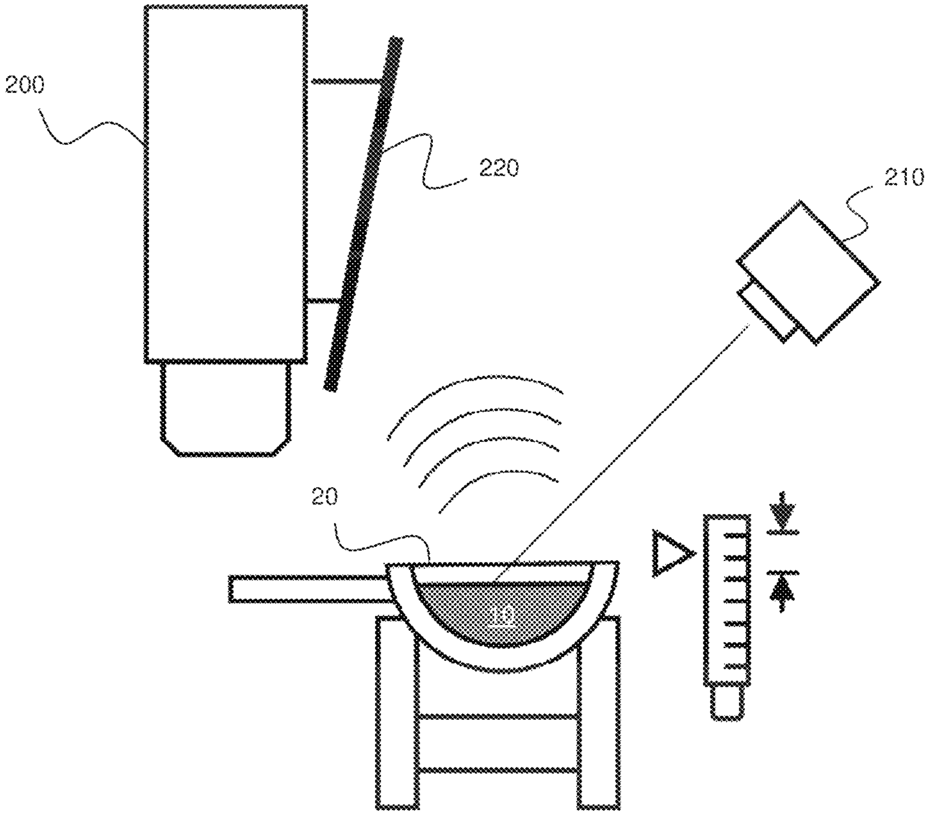
FIG. 6 illustrates an example embodiment in which a heat shield is employed to protect the LIBS measurement head when the LIBS measurement head is parked laterally to a crucible support.

FIG. 6 illustrates a system state in which the LIBS measurement head 200 is parked in a lateral position to permit non-contact temperature sensing of a molten metal sample via a temperature sensor 210. The LIBS measurement head 200 includes a heat shield 220 that is positioned to thermally shield the LIBS measurement head 200 from heat radiating from the crucible 20. The figure illustrates a non-limiting example implementation in which the heat shield 220 is secured to the LIBS measurement head 200 such that the heat shield 220 resides between the LIBS measurement head 200 and the crucible 20 when the LIBS measurement head 200 resides in the parked position.

In some example embodiments, one or more calibration devices may be employed to calibrate the LIBS measurement head 200 when the LIBS measurement head 200 resides in a parked position. FIG. 1 illustrates an example implementation in which the system includes a calibration station 500 that can be accessed by the LIBS measurement head 200 in a parked position 201. As shown in FIG. 1, the calibration station 500 may be interfaced with (e.g. controlled by) the processing and control circuitry 100, as shown at 502. In cases in which the support 50 is a mobile support and the mobile LIBS system is employed in a non-laboratory setting, the integrated calibration station can be employed to ensure accurate operation of the system, even in the presence of challenging environmental conditions, such as high temperatures and dust.

For example, during some implementations of LIBS analysis, it can be beneficial to ensure a consistent distance between the liquid metal surface and the excitation and detection optics (e.g. the distal region of the LIBS measurement head 200). This distance can be controlled with any suitable type of distance sensor that provides feedback to the mechanical translation mechanism of the LIBS measurement head 200. However, during a measurement run, the LIBS measurement head can be subjected to significant variations in ambient temperature as well as heating due to thermal radiation from the sample and the measurement ladles, and this heating can be exacerbated in non-laboratory settings, such a pot room of an aluminum smelter. In order to ensure rapid and repeatable measurements, a calibration station may be incorporated into the system (e.g. supported with the LIBS system by a common mobile support structure) that allows a distance sensor to be calibrated prior to a given (optionally, each) measurement, thus correcting, at least in part, for thermal drift in the system.

Figure 7A:
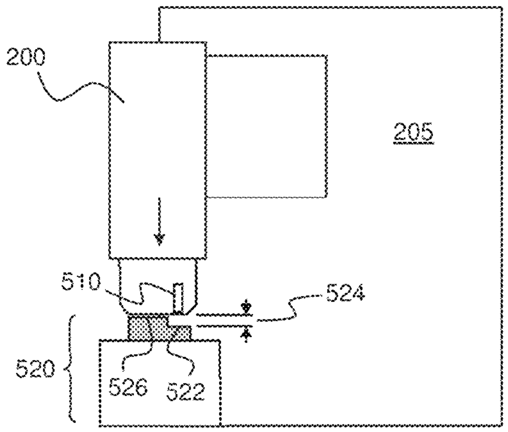
FIGS. 7A-7C illustrate example calibration subsystems for performing calibration operations on the LIBS measurement head in between measurements.

An example implementation of a calibration station for calibrating a distance sensor is shown in FIG. 7A. The LIBS measurement head 200 includes a distance sensor 510, and a remainder of the LIBS measurement subsystem (e.g. including source and detection components) is schematically illustrated at 205. The LIBS measurement head 200 is shown in a parked position, remote from a crucible, with the distance sensor residing over a calibration reference surface 522 of a distance sensor calibration station 520. The calibration reference surface 522 provides a fixed reference location that can be employed to calibrate the distance sensor 510. For example, the LIBS measurement head 200 can be lowered (manually or robotically) in a direction parallel to the optical axis of the LIBS measurement head 200 until the LIBS measurement head 200 contacts a contact location 526 (this contact can be detected, for example, via a contact sensor such as an electrically conductive or mechanical contact sensor). Contact of the distal end of the LIBS measurement head 200 (or another suitable location within a distal region of the LIBS measurement head) with the contact location 526 of the distance sensor calibration station 520 ensures that distance sensor 510 and the reference surface 522 are separated by a known distance, thereby facilitating calibration of the distance sensor 510 via the interrogation of the reference surface by the distance sensor 510.

Figure 7B:
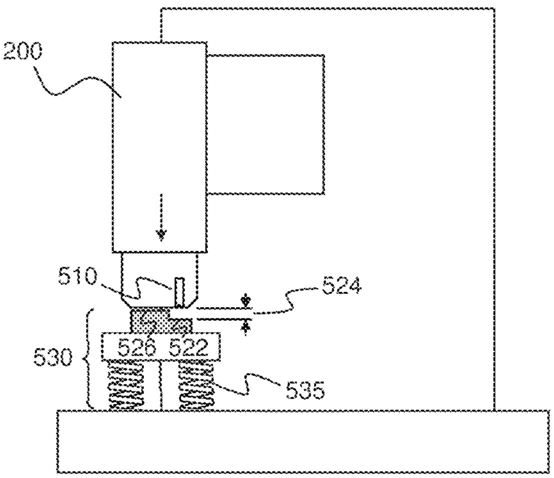

FIG. 7B illustrates an alternative example implementation in which the distance sensor calibration station 530 is elastically biased, for example by one or more springs 535 or other suitable elastically deformable components, which can be employed to ensure that a known spatial offset is maintained between the distance sensor 510 and the reference surface 522 when the LIBS measurement head 200 is lowered further after having made contact with the contact surface 526, without having to rely on a separate contact sensor. The one or more springs 535 can also advantageously ensure accurate and repeatable levelling of the reference surface 522 relative to the LIBS measurement head 200 when the contact location 526 is provided as a contact surface or provided as plurality of contact locations defining a contact plane.

Figure 7C:
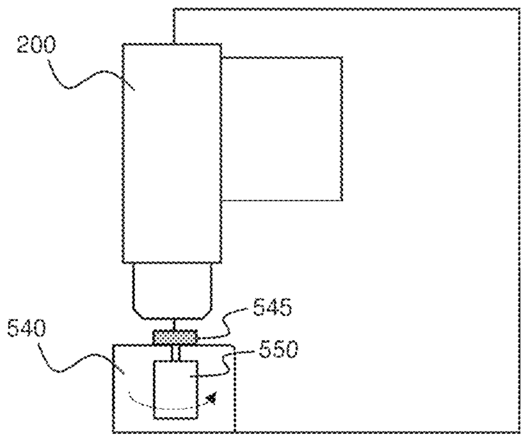

FIG. 7C illustrates an example of a calibration station 540 for calibrating the optical response of the LIBS subsystem. The example calibration station 540 supports (e.g. via bracket) an interchangeable solid reference sample of reference material 545 of a known chemical concentration in order to correct for drift in the signal response of the LIBS subsystem. For example, analysis of the solid reference sample is compared with a previous analysis of the same reference sample and the system is calibrated to accommodate for observed differences in the concentration of the detected reference material. In some example implementations, the calibration station may advantageously facilitate a translating and/or rotating functionality to ensure that the reference material can be measured at a new location when a subsequent drift correction measurement is performed. A rotation and/or translation function can also be used to interrogate multiple reference materials mounted on the calibration station. This rotation and/or translation of the calibration reference station 540 may be autonomously controlled by the control and processing circuitry 100, as shown, for example at 502 in FIG. 1. FIG. 7C illustrates an example implementation in which a motor 550 is controlled to rotate the solid reference sample relative to a LIBS interrogation location when performing subsequent calibrations.

In some example embodiments, the calibration station may facilitate multiple calibrations, including, but not limited to, the calibration of a distance sensor and the use of one or more reference materials to calibrate the response of the LIBS measurement system. In some example implementations, one or more calibration steps may be autonomously performed when one or more conditions are met, such as, for example, after a selected number of samples have been measured, after a detected change in ambient conditions, and/or after an elapsed time.

Referring again to FIG. 1, the LIBS subsystem is supported on a support 50. As noted above, in some example implementations, the support 50 may be a mobile (portable) support. For example, the support 50 may be a manually-movable cart (pushcart) or a motorized vehicle (e.g. a cart having battery-powered translation), including a semi-autonomous (self-driving) vehicle. In some example embodiments, a portable LIBS system may be battery powered. As described above, the present example methods that involve passive cooling and temperature monitoring prior to initiation of a LIBS measurement are well-suited to a battery-powered implementation due to the absence of active heating sources that have high power requirements.

Figure 8:
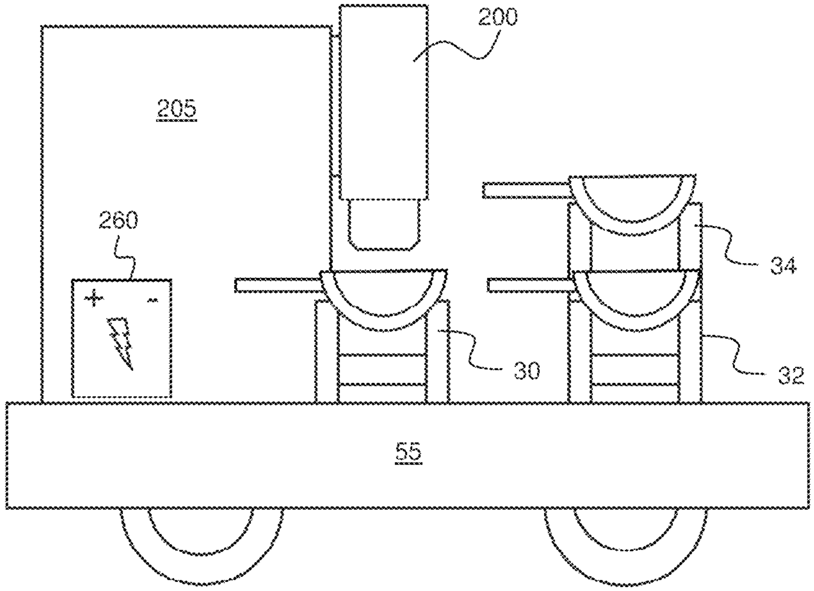
FIG. 8 illustrates an example mobile LIBS measurement system that includes a battery power source.
Figure 9:
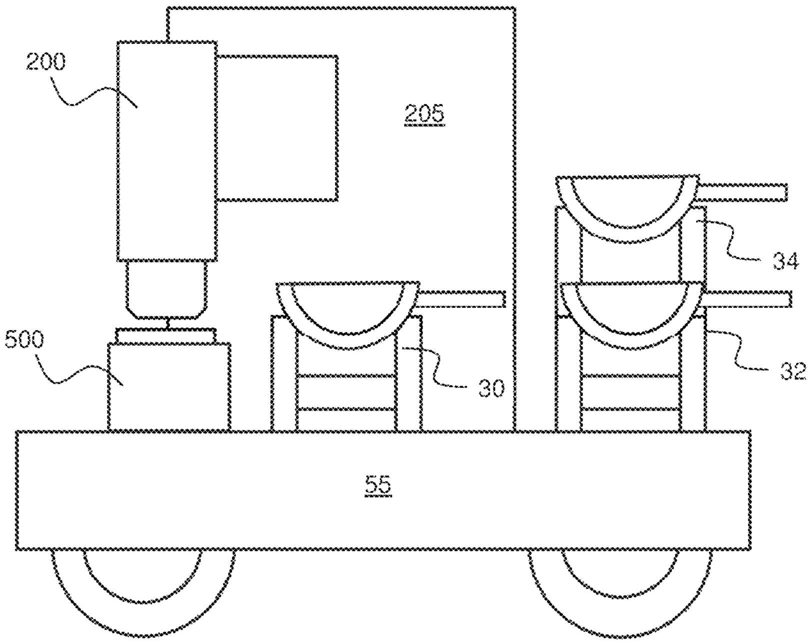
FIG. 9 illustrates an example mobile LIBS measurement system that includes a calibration station.

FIG. 8 illustrates an example of a mobile LIBS measurement system that includes a LIBS subsystem (200, 205), a primary crucible support 30 for supporting a crucible in a measurement position for performing LIBS measurements, and at least one additional crucible support for supporting additional crucibles (the example system includes two additional crucible supports 32 and 34) during passive cooling prior to being used for LIBS measurements, a battery source 260, and a mobile support 55. FIG. 9 illustrates the inclusion of the calibration station 500 in a mobile configuration, where the calibration station 500, the LIBS subsystem and one or more crucible supports (e.g. crucible supports 30, 32 and 34) are supported by the mobile support 55.

Although many of the present example embodiments relate to a portable LIBS system, it is noted that in other example embodiments, the support that supports the LIBS measurement subsystem may be a fixed support. For example, any of the present example systems or methods may be adapted to a non-portable configuration, such as a system configuration suitable for implementation at a furnace, launder or other fixed source of liquid metal, either in a plant/smelter or a laboratory setting. In such settings, the sampling may be advantageously automated (e.g., by using a robot arm).

Furthermore, while many of the preceding example implementations employ the passive cooling of the molten metal sample prior to LIBS analysis, and/or the passive cooling of an overheated crucible prior to further use, it will be understood that some implementations may employ active heating and/or active cooling. For example, in some example implementations, forced air may be employed to cool an overheated empty crucible residing on a crucible support. Feedback from a temperature sensor measuring the temperature of the crucible may be employed to control the cooling device to bring the empty crucible to a temperature that satisfies the crucible temperature criteria. Active heating may also optionally be employed to pre-heat one or more crucibles. For example, in some example implementations, one or more crucible supports may include a heat source (e.g. an inductive or resistive heater or a gas burner). Feedback from the temperature sensor measuring the temperature of the crucible may be employed to control the heat source to bring the empty crucible to a temperature that satisfies the crucible temperature criteria. In some example implementations, the system may include both active heating and cooling devices to control the temperature of one or more crucibles.

In other example implementations, active heating (such as inductive heating) and or cooling (such as forced air cooling) may be employed, in combination with the monitored temperature of the molten metal sample with the crucible, to stabilize the temperature of the molten metal sample prior to, or during, LIBS measurements.

The embodiments of the present disclosure can be applied to a variety of metals and metal alloys such as but not limited to aluminum, steel, steel alloys, iron, iron alloys, copper, zinc, lead and other metals and metal alloys in their liquid state and can be useful in industrial settings and applications as mentioned above.

It will be understood that the present disclosure is not intended to be limited to analysis of any particular elements and can be used both to determine concentration of the main components in the metal or alloy sample, or trace components. Accordingly, in some embodiments the method and/or apparatus is for determining in the liquid metal or alloy sample the true bulk concentration of one or more elements selected from Aluminum, Silicon, Phosphorus, Sulphur, Chloride, Calcium, Magnesium, Sodium, Titanium, Vanadium, Chromium, Manganese, Iron, Cobalt, Nickel, Copper, Zinc, Zirconium, Strontium, Niobium, Molybdenum, Ruthenium, Rhodium, Palladium, Silver, Cadmium, Tin, Antimony, Wolfram, Rhenium, Iridium, Platinum, Gold, Mercury, Lead and Bismuth. The method is also suitable for quantifying very light impurity elements such as Hydrogen, Lithium, Beryllium, Boron and Carbon that are difficult to detect with certain other analysis methods. Furthermore, it will be understood that trace impurities may be introduced to the liquid metal from the sampling equipment itself, e.g. sampling ladles and measurement crucibles. The present disclosure applies equally to measurement and identification of such contaminants.

Referring again to FIG. 1, the LIBS system generally includes a means of excitation and detection for generating and receiving atomic emission from the sample. This includes but is not limited to all variations of laser-induced plasma excitation methodology known in the art, including but not limited to the use of conventional LIBS methods, LIBS with dual collinear or non-collinear pulses, combined LIBS/electrical discharge methods, or the like.

In some example embodiments, the spectral analysis is based on a LIBS method where one or more laser pulses in sequence are directed to the sample surface through excitation optics, and light emitted from the sample is received through receiving optics and transmitted to a detector for recording spectral information of the detected light. Optical detection methods and subsequent processing of detected emission are as such known to the person skilled in the art. From the spectral information one or more emission peaks are then analyzed and typically compared to calibration values in order to obtain quantitative determination of one or more elements.

The excitation optics and receiving optics of the LIBS measurement subsystem may be fully separate or partly comprising the same optical elements. In a preferred implementation, the excitation means and receiving optics may be accurately positioned at a pre-determined distance from the sample surface for each individual excitation event. The accuracy of this positioning over time during field operation is advantageously maintained using a distance calibration function as described above.

A pulsed excitation laser employed in various example embodiments may be generally of conventional type as is used in present day LIBS configurations. According to the invention, stable excitation conditions may be provided with the optical excitation configured such that a sufficiently large and reproducible volume of the liquid metal sample is ablated during excitation and such that the chemical composition of this ablated fraction of the sample is representative of the composition of the whole sample.

In some embodiments a stream of inert gas, such as argon, helium or nitrogen, is fed from a source, such as a pressurized canister mounted on the same portable support as the LIBS system, through one or more gas channels to the vicinity of the sampling point to maintain an inert atmosphere during the LIBS measurement.

In some example embodiments, the receiving optics of the LIBS measurement head may include more than one lens, with the lenses optionally arranged radially around the point of contact of the laser pulse and sample surface. Light collected by the one 10 or more receiving optics can be transferred via fiber optics or other optical transmission means to the same spectrometer or to different spectrometers (for example, each lens in a plurality if lenses can transfer light to its respective spectrometer). In some embodiments such plurality of spectrometers may be configured so that each spectrometer collects emission at a limited wavelength range, so that the plurality of spectrometers together covers the entire desired wavelength range. In some embodiments, spectroscopic detection may also comprise detection of selected wavelength bands using one or more suitable bandpass filters and optical sensors.

Referring again to FIG. 1, an example implementation of control and processing circuitry 100 is shown, which includes one or more processors 110 (for example, a CPU/microprocessor), bus 105, memory 115, which may include random access memory (RAM) and/or read only memory (ROM), a data acquisition interface 120, a display 125, external storage 130, one more communications interfaces 135, a power supply 140, and one or more input/output devices and/or interfaces 145 (e.g. a speaker, a user input device, such as a series of pushbuttons, a joystick, a keyboard, a keypad, a mouse, a position tracked stylus, a position tracked probe, a foot switch, and/or an acoustic transducer for capturing speech commands).

The preceding example methods may be autonomously implemented according to modules 155, 160 and 165 of the control and processing circuitry 100. For example, the measurement of the temperature of the empty crucible, the monitoring of the temperature of the molten metal sample, and the evaluation of the crucible temperature criteria and the measurement temperature criteria, may be performed according to executable instructions implemented by the temperature monitoring module 155. Robotic control of the LIBS measurement head (and optionally one or more components of the calibration station 500) may be controlled according to the robotic actuation module 160, and LIBS measurement acquisition and data processing may be performed according to the LIBS measurement module 165.

It is to be understood that the example system shown in FIG. 1 is illustrative of a non-limiting example embodiment, and is not intended to be limited to the components shown. Furthermore, one or more components of control and processing circuitry 100 may be provided as an external component that is interfaced to a processing device.

For example, the control and processing circuitry may include a local computing subsystem that includes a first set of components supported by the support 50, where the local computing subsystem is connectable, through a network, to one or more external computing devices. The network may include a local and/or external network, where one or more segments of the network may be wireless. For example, in some implementations, data locally obtained and optionally processed by local computing subsystem may be transmitted to one or more external computing devices, such as, for example, an external control system residing within or remote from a metal processing plant, or, for example, one or more mobile computing devices such as mobile phones, laptops and tablet computing devices. Examples of such data include raw data, analysis results and/or status of equipment (which may include, for example, environment variables, error messages, alerts, or other measures or indications). The communication between the local computing subsystem and the one or more external computing devices may be unidirectional (e.g. for autonomous uploading of data to the remote computing devices) or bidirectional. In some example implementations, the local computing subsystem may be configured to receive one or more portable computing device in a "docked" configuration for transmitting data through a wired or wireless connection.

Although only one of each component is illustrated in FIG. 1, any number of each component can be included in the control and processing circuitry 100. For example, a computer typically contains a number of different data storage media. Furthermore, although bus 105 is depicted as a single connection between all of the components, it will be appreciated that the bus 105 may represent one or more circuits, devices or communication channels (which may optionally include wireless communications channels) which link two or more of the components. For example, in personal computers, bus 105 often includes or is a motherboard. Control and processing circuitry 100 may include many more or less components than those shown.

Control and processing circuitry 100 may be implemented as one or more physical devices that are coupled to processor 110 through one of more communications channels or interfaces. For example, control and processing circuitry 100 can be implemented using application specific integrated circuits (ASICs). Alternatively, control and processing circuitry 100 can be implemented as a combination of circuitry and software, where the software is loaded into the processor from the memory or over a network connection.

Some aspects of the present disclosure can be embodied, at least in part, in software. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete circuitry components as large-scale integrated circuits (LSI's), application-specific integrated circuits (ASIC's), or firmware such as electrically erasable programmable read-only memory (EEPROM's) and field-programmable gate arrays (FPGAs).

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine readable medium includes any mechanism that provides (i.e., stores and/or transmits) information in a form accessible by a machine (e.g., a computer, network device, personal digital assistant, manufacturing tool, any device with a set of one or more processors, etc.).

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. As used herein, the phrases "computer readable material" and "computer readable storage medium" refer to all computer-readable media, except for a transitory propagating signal per se.

EXAMPLES

The following examples are presented to enable those skilled in the art to understand and to practice embodiments of the present disclosure. They should not be considered as a limitation on the scope of the disclosure, but merely as being illustrative and representative thereof.

Figure 10:
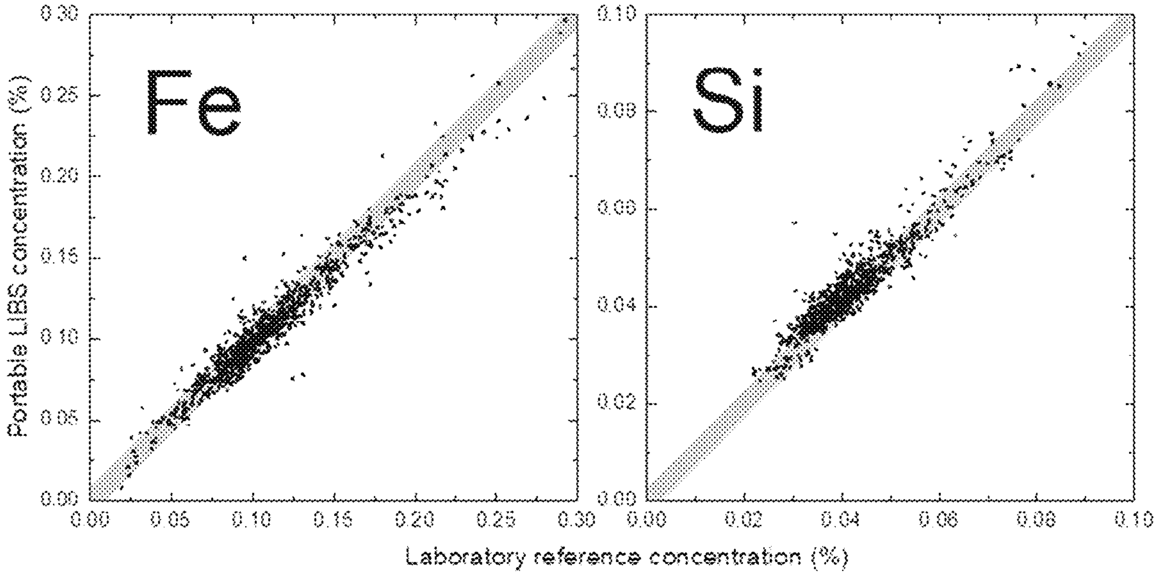
FIG. 10 shows the correspondence between elemental impurity analysis performed on (i) liquid aluminum samples using a portable LIBS system and (ii) solid aluminum samples using a laboratory-based spark-OES system.

FIG. 10 shows results from analysis of liquid aluminum samples from several hundred reduction cells, performed using passive cooling and automated initiation of LIBS measurements according to an embodiment of the present disclosure, compared with results from laboratory spark-OES analysis of conventionally prepared solid samples. Data from several primary aluminum smelters has been combined. The measurements were performed using a portable battery-powered LIBS analyzer mounted on an electric vehicle, incorporating a distance calibration function as described above and three interchangeable measurement ladles.

Prior to introduction of a molten aluminum sample into a measurement crucible, the measurement crucible preheated to a temperature satisfying the crucible temperature criteria. After introducing a given molten aluminum sample into the measurement crucible, the temperature of the molten aluminum sample was monitored using a non-contact thermometer while passive cooling the molten aluminum sample, without performing active heating or active cooling of the crucibles. The LIBS measurement was carried out upon fulfilment of measurement temperature criteria as described above.

As demonstrated in FIG. 10, the agreement (one standard deviation) between the results from the portable LIBS measurements and the results from the laboratory reference measurements was better than 90 ppm in the case of Fe and better than 30 ppm in the case of Si, as illustrated schematically by the widths of the gray lines in the figure.

Measurements were typically collected from up to 50 reduction cells in sequence, where the features of the present example portable LIBS system enabled an average cycle time of around 90 seconds per cell. This included the time for sampling aluminum from the cells, cooling of the aluminum to satisfy the measurement temperature criteria, carrying out the LIBS measurement, and transportation of the analyzer between cells using the electric vehicle.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

The invention claimed is:

1. A method of performing laser-induced breakdown spectroscopy (LIBS) on a molten sample during cooling of the molten sample, the method comprising:
   - monitoring a temperature of the molten sample during cooling of the molten sample within a crucible, and comparing the temperature of the molten sample to measurement temperature criteria; and
   - determining that the temperature of the molten sample satisfies the measurement temperature criteria and initiating a LIBS measurement on the molten sample,
   - characterized by the further steps of, prior to introduction of the molten sample:
   - measuring, one or more times, a temperature of the crucible, the crucible being in a preheated state and absent of the molten sample, and comparing the temperature of the crucible to crucible temperature criteria; and
   - determining that the temperature of the crucible satisfies the crucible temperature criteria and providing an indication that the crucible is ready to receive the molten sample;
   - wherein the crucible temperature criteria is configured such that the molten sample cools by fewer than 50° C. during the LIBS measurement.

2. The method according to claim 1 wherein the crucible temperature criteria comprises a minimum crucible temperature, such that the crucible temperature criteria is satisfied when the minimum crucible temperature is exceeded.

3. The method according to claim 2 wherein the minimum crucible temperature resides between 100° C. and 60% of the melting point temperature of the molten sample in degrees Celsius.

4. The method according to claim 2 wherein the minimum crucible temperature resides between 15% of the melting point temperature of the molten sample and 60% of the melting point temperature in degrees Celsius.

5. The method according to claim 1 wherein the crucible temperature criteria is satisfied when the temperature of the crucible resides within a crucible temperature range.

6. The method according to claim 5 wherein a maximum crucible temperature of the crucible temperature range is defined such that when the temperature of the crucible equals the maximum crucible temperature and the molten sample is added to the crucible, the temperature of the molten sample satisfies the measurement temperature criteria within 1 minute.

7. The method according to claim 5 wherein a maximum crucible temperature of the crucible temperature range is defined such that when the temperature of the crucible equals the maximum crucible temperature and the molten sample is added to the crucible, the temperature of the molten sample satisfies the measurement temperature criteria within 30 seconds.

8. The method according to claim 6 wherein the maximum crucible temperature resides between 50% of the melting point temperature of the molten sample in degrees Celsius and 90% of the melting point temperature.

9. The method according to claim 1 wherein the measurement temperature criteria is selected such that the LIBS measurement is performed within a pre-selected measurement temperature range.

10. The method according to claim 1 wherein the measurement temperature criteria comprises a pre-selected measurement temperature, and the LIBS measurement is initiated immediately after (i) determining that the temperature of the molten sample equals the pre-selected measurement temperature and (ii) positioning a LIBS measurement head over the crucible.

11. The method according to claim 1 wherein the measurement temperature criteria comprises a pre-selected measurement temperature, and the LIBS measurement is performed after determining that the temperature of the molten sample equals the pre-selected measurement temperature.

12. The method according to claim 11 wherein the pre-selected measurement temperature exceeds the melting point temperature of the molten sample by an amount ranging from 5% to 25% of the melting point temperature in degrees Celsius.

13. The method according to claim 1 wherein the measurement temperature criteria comprises a pre-selected measurement temperature range, that the LIBS measurement is performed while the temperature of the molten sample resides within the pre-selected measurement temperature range.

14. The method according to claim 1 wherein the measurement temperature criteria is configured such that the temperature of the molten sample during the LIBS measurement exceeds the temperature of the crucible when the crucible temperature criteria is satisfied.

15. The method according to claim 1 wherein the crucible is preheated by a previously measured molten sample, wherein the previously measured molten sample is discarded prior to measuring the temperature of the crucible.

16. The method according to claim 1 wherein the molten sample comprises aluminum and wherein the crucible is preheated by contact with a cryolite crust formed on the top of a reduction cell.

17. The method according to claim 1 wherein the temperature of the crucible and the temperature of the molten sample are measured using a common temperature sensor.

18. The method according to claim 1 wherein the temperature of the crucible and the temperature of the molten sample are measured in absence of contact.

19. The method according to claim 1 wherein the crucible is supported by a crucible support during LIBS measurement.

20. The method according to claim 19 wherein LIBS measurements are performed by a LIBS subsystem, and wherein a measurement head of the LIBS subsystem is movable from a parked position to an operative position in which the measurement head resides above the crucible support, and wherein a heat shield is positioned to thermally shield the measurement head from heat radiating from the crucible when the measurement head resides in the parked position.

21. The method according to claim 1 wherein the crucible is a metallic crucible.

22. The method according to claim 21 wherein the crucible is formed from structural steel.

23. The method according to claim 1 wherein a heat capacity of the crucible resides between 400 and 500 J/K.

24. The method according to claim 1 wherein a thermal conductivity of the crucible resides between 40 and 50 W/m-K.

25. The method according to claim 5 wherein the crucible is a first crucible, the molten sample is a first molten sample, the method further comprising:

discarding the first molten sample from the first crucible;

measuring a temperature of the first crucible;

determining that the temperature of the first crucible fails to satisfy the crucible temperature criteria due to an excessively high temperature;

replacing the first crucible with a second crucible having a temperature less than that of the first crucible; and employing the second crucible to perform LIBS measurements on a second molten sample while cooling the first crucible.

26. The method according to claim 25 wherein the first crucible is supported by a primary crucible support during the LIBS measurement performed on the first molten sample; and wherein, after replacing the first crucible with the second crucible, the first crucible is placed on a secondary crucible support for cooling.

27. The method according to claim 25 further comprising, prior to replacing the first crucible with the second crucible:

preheating the second crucible;

monitoring a temperature of the second crucible; and indicating when the second crucible satisfies the crucible temperature criteria.

28. The method according to claim 25 further comprising:

employing the second crucible to perform LIBS measurements on one or more additional molten samples;

emptying the second crucible;

measuring a temperature of the second crucible;

determining that the temperature of the second crucible fails to satisfy the crucible temperature criteria due to an excessively high temperature; and replacing the second crucible with a crucible selected from:

the first crucible; and a third crucible; and employing the selected crucible to perform LIBS measurements on another additional molten sample.

29. The method according to claim 1 wherein the LIBS measurement is performed by a LIBS system residing on a portable support structure, and wherein the LIBS system is powered by a battery.

30. The method of claim 1, the method further comprising:

preheating a crucible;

introducing a molten sample into the crucible.

31. A system for performing laser-induced breakdown spectroscopy (LIBS), the system comprising:

a laser-induced breakdown spectroscopy (LIBS) subsystem;

a first crucible;

a primary crucible support for supporting the first crucible holding the sample during measurement;

a second crucible;

a secondary crucible support capable of supporting and cooling the second crucible; and a mobile support structure configured to support said LIBS subsystem, said primary crucible support and said secondary crucible support, wherein said primary and secondary crucible supports and said first and second crucibles are configured so the first crucible can be replaced by said second crucible, for performing LIBS measurements on a molten sample residing in the second crucible in the primary crucible support and the first crucible can be placed in the secondary crucible support for cooling;

a temperature sensor; and processing circuitry operatively coupled to said temperature sensor and said LIBS subsystem, said processing circuitry comprising at least one processor and associated memory, said memory comprising instructions executable by said processor for performing operations comprising:

employing said temperature sensor to monitor a temperature of a molten sample during cooling of the molten sample within a crucible; and comparing the temperature of the molten sample to measurement temperature criteria, and determining that the molten sample satisfies the measurement temperature criteria and controlling said LIBS subsystem to initiate a LIBS measurement on the molten sample.

32. The system according to claim 31 wherein said processing circuitry is further configured to perform the following operations prior to introduction of the molten sample into a crucible:

employing said or another temperature sensor to measure a temperature of the crucible, the crucible being preheated; and after determining that the temperature of the crucible satisfies crucible temperature criteria, providing an indication that the crucible is ready to receive the molten sample;

wherein the crucible temperature criteria is configured such that the molten sample cools by fewer than 50° C. during the LIBS measurement.

33. The system according to claim 31, wherein said LIBS subsystem is connectable to a battery.

34. A portable system for performing laser-induced breakdown spectroscopy (LIBS), the portable system comprising:

a laser-induced breakdown spectroscopy (LIBS) subsystem comprising a measurement head, said LIBS subsystem being connectable to a battery;

a first crucible;

a primary crucible support, wherein said measurement head of said LIBS subsystem is movable from a parked position to an operative position in which said measurement head resides above said primary crucible support for performing LIBS measurements on a molten sample residing in said first crucible supported by said primary crucible support;

a second crucible;

a secondary crucible support capable of supporting and cooling said second crucible; and a mobile support structure configured to support said LIBS subsystem, said primary crucible support and said secondary crucible support, wherein said crucible supports and said first and second crucibles are configured so the first crucible can be replaced by said second crucible, for performing LIBS measurements on a molten sample residing in the second crucible in said primary crucible support, and the first crucible can be placed in the secondary crucible support for cooling, system further comprising:

a temperature sensor configured to monitor a temperature of the crucible residing in said primary crucible support when said measurement head is in the parked position; and processing circuitry operatively coupled to said temperature sensor, said processing circuitry comprising at least one processor and associated memory, said memory comprising instructions executable by said processor for performing operations comprising:

employing said temperature sensor to measure a temperature of the crucible supported by said primary crucible support; and after determining that the temperature of the crucible fails to satisfy crucible temperature criteria due to an excessively high temperature, providing an indication that the crucible should be cooled in said secondary crucible support prior to use.

35. The portable system according to claim 34, wherein said first crucible and said second crucible are metallic.

36. The portable system according to claim 34, wherein said first crucible and said second crucible are formed from structural steel.

37. The portable system according to claim 34, wherein heat capacities of said first crucible and said second crucible reside between 400 and 500 J/K.

38. The portable system according to claim 34, wherein thermal conductivities of said first crucible and said second crucible reside between 40 and 50 W/m-K.

39. A portable system for performing laser-induced breakdown spectroscopy (LIBS), the portable system comprising:

a laser-induced breakdown spectroscopy (LIBS) subsystem comprising a measurement head, said LIBS subsystem being connectable to a battery;

an integrated calibration apparatus; and a mobile support structure configured to support said LIBS subsystem and said integrated calibration apparatus;

said measurement head of said LIBS subsystem being movable, from an operative position in which said measurement head resides above a first crucible for performing LIBS measurements on a molten sample residing in the first crucible, to a calibration position suitable for performing calibrating measurements suitable for calibrating at least one parameter of said LIBS subsystem, wherein said measurement head comprises a distance sensor, and wherein said integrated calibration apparatus is an integrated distance sensor calibration apparatus, said integrated distance sensor calibration apparatus comprising a contact location and a target location, said contact location being located on said integrated calibration apparatus such that when said measurement head resides at the calibration position and is contacted with said contact location after lowering said measurement head along a direction parallel to an optical axis of said measurement head, a known spatial offset resides between said distance sensor and said target location, thereby facilitating calibration of said distance sensor.

40. The portable system according to claim 39 wherein said integrated distance sensor calibration apparatus is elastically biased such that the known spatial offset is maintained when said measurement head is moved along the direction after having made contact with said contact location.

41. The portable system according to claim 39 further comprising:

a primary crucible support for supporting the first crucible while performing the LIBS measurements; and a secondary crucible support capable of supporting and cooling a second crucible.

* * * * *